Oct. 5, 1943. C. LAUGHLIN ET AL Plant Pat. 602
LILY PLANT
Filed Feb. 1, 1943
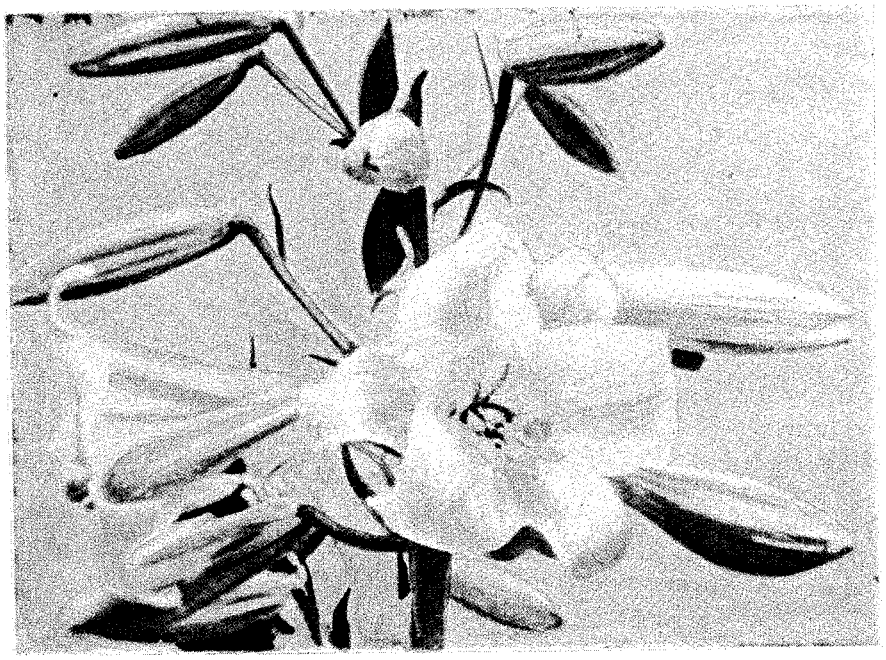
INVENTORS
Cowden Laughlin
Lester McCosh Laughlin Patented Oct. 5, 1943

Plant Pat. 602

UNITED STATES PATENT OFFICE

602

LILY PLANT

Cowden Laughlin, Vashon, and Lester McCosh Laughlin, Bellingham, Wash.

Application February 1, 1943, Serial No. 474,314

1 Claim. (Cl. 47—60)

Our new discovery is a new hybrid of the regal lily. It is an improvement over the regal lily in that it has a beautiful yellow color; a waxy corolla and a later blooming season.

In 1926 and 1927, we planted a very large quantity of the seed of *Lilium regale*. Part of this seed had come, indirectly, from seed which had been pollinated and disseminated by Luther Burbank. When the bulbs matured and bloomed, we found one which had a beautiful yellow color.

We segregated this bulb from the others and tested and observed it for several years. Seed from this lily has been planted for several successive years, but the result is always the regular, typical regal lily. However, by asexual reproduction the same, identical parent plant is invariably obtained.

The flowers are somewhat shorter than those of *Lilium regale*. The petals are thicker and wax like. The color is a beautiful bronze or ivory cream which changes imperceptibly into a canary yellow and finally into a decided yellow deep in the throat. The backs of the petals have a stronger touch of bronze, especially along the midrib, but almost no indication of the usual red back of the regal lily. No part of the flower is white.

The following is a detailed description of the lily:

Bulb: The bulbs are firm and have a coppery cream and pink color.

Height: It is from 3–4½ feet tall or taller in good ground, but not so tall as the regal.

Foliage: The stem and leaves are very similar to those of *Lilium regale*, but both are of a lighter green color.

Buds: The buds are slightly shorter than those of the regal, with peduncles which are quite short. Each peduncle has a short bract or leaflet. The color of the bud is a light greenish yellow.

Petals: The petals are thicker than those of the regal. They are recurved and of a waxy texture. When the flowers first open they have a greenish color which entirely disappears in a day or two, changing into a beautiful ivory cream or yellow. The deep throat is decidedly yellow. The backs of the petals have a stronger color, approaching a bronze. There is almost no indication of the usual red back of the regal.

Odor: The odor is not so strong and is consequently, more pleasant.

Date of blooming: The time of blooming is from two to three weeks later than the regular regal lily, in the vicinity of Seattle.

Having thus disclosed our discovery, we claim:

A new and distinct variety of hardy lily plant of the regal type, characterized by the yellow color, wax-like texture and relatively late blooming date of its flowers, substantially as herein disclosed.

COWDEN LAUGHLIN.
LESTER McCOSH LAUGHLIN.